US009775640B2

(12) United States Patent
Dosher et al.

(10) Patent No.: US 9,775,640 B2
(45) Date of Patent: Oct. 3, 2017

(54) SURGICAL DEVICE

(75) Inventors: Jesse A. Dosher, Shoreline, WA (US);
Diana C. W. Friedman, Seattle, WA (US); Daniel Glozman, Kefar Adummim (IL); Blake Hannaford, Seattle, WA (US); Aylin Z. Kim, Seattle, WA (US); Louis Kim, Seattle, WA (US); Thomas S Lendvay, Seattle, WA (US); Kristen S. Moe, Seattle, WA (US); James S. Pridgeon, Seattle, WA (US); Jacob Rosen, Santa Cruz, CA (US); Laligam Sekhar, Seattle, WA (US)

(73) Assignee: SPI Surgical, Inc., Seattle, WA (US)

( * ) Notice: Subject to any disclaimer, the term of this patent is extended or adjusted under 35 U.S.C. 154(b) by 427 days.

(21) Appl. No.: 12/943,745

(22) Filed: Nov. 10, 2010

(65) Prior Publication Data

US 2011/0118543 A1 May 19, 2011

(51) Int. Cl.
| *A61B 1/00* | (2006.01) |
| *A61B 17/34* | (2006.01) |
| *A61B 18/22* | (2006.01) |
| *A61B 17/00* | (2006.01) |
| *A61B 17/29* | (2006.01) |
| *A61N 7/02* | (2006.01) |

(52) U.S. Cl.
CPC .......... *A61B 17/3421* (2013.01); *A61B 18/22* (2013.01); *A61B 2017/003* (2013.01); *A61B 2017/2906* (2013.01); *A61B 2017/2908* (2013.01); *A61B 2017/3447* (2013.01); *A61N 7/022* (2013.01)

(58) Field of Classification Search
CPC .......... A61B 1/00; A61B 1/008; A61B 1/005; A61B 17/00; A61B 19/00; A61B 17/34; A61M 37/00
USPC .... 606/1; 600/104, 106, 107, 114, 128, 129, 600/139, 141, 142, 146, 149, 153, 154, 600/155, 156
See application file for complete search history.

(56) References Cited

U.S. PATENT DOCUMENTS

| 3,521,620 | A | * | 7/1970 | Cook ............................ 600/585 |
| 4,936,312 | A | * | 6/1990 | Tsukagoshi ................... 600/562 |
| 5,372,587 | A | * | 12/1994 | Hammerslag et al. .... 604/95.04 |
| 6,162,239 | A | | 12/2000 | Manhes |
| 6,309,345 | B1 | | 10/2001 | Stelzer et al. |
| 2004/0138525 | A1 | | 7/2004 | Saadat et al. |

(Continued)

OTHER PUBLICATIONS

PCT International Preliminary Report and Written Opinion of PCT Application No. PCT/US2010/056322 mailed May 24, 2012.

*Primary Examiner* — William Thomson
*Assistant Examiner* — Victor Shapiro
(74) *Attorney, Agent, or Firm* — Wilson Sonsini Goodrich & Rosati

(57) ABSTRACT

A surgical device that has an external sheath having a proximal end and a distal end for insertion through an opening of a body and a plurality of tool components extending from the distal end of the external sheath. The tool components are independently deflectable with respect to each other and with respect to the external sheath and removable from the device without requiring withdrawal of the sheath through the opening of the body. The external sheath is flexible and deflectable intermediate the distal and proximal ends. This permits the device to be steered in a curvilinear manner towards a surgical target.

50 Claims, 5 Drawing Sheets

(56) References Cited

U.S. PATENT DOCUMENTS

| | | |
|---|---|---|
| 2004/0249367 A1 | 12/2004 | Saadat et al. |
| 2005/0059960 A1 | 3/2005 | Simaan et al. |
| 2007/0016174 A1 | 1/2007 | Millman et al. |
| 2008/0027464 A1 | 1/2008 | Moll et al. |
| 2008/0045803 A1* | 2/2008 | Williams et al. ............. 600/204 |
| 2008/0065105 A1 | 3/2008 | Larkin et al. |
| 2008/0065108 A1 | 3/2008 | Diolaiti |
| 2008/0071288 A1 | 3/2008 | Larkin et al. |
| 2008/0188868 A1 | 8/2008 | Weitzner et al. |
| 2008/0243064 A1 | 10/2008 | Stahler et al. |
| 2008/0269727 A1 | 10/2008 | Lee |
| 2009/0054728 A1 | 2/2009 | Trusty |
| 2009/0137952 A1 | 5/2009 | Ramamurthy et al. |
| 2009/0259105 A1 | 10/2009 | Miyano et al. |

\* cited by examiner

SURGICAL DEVICE

PRIORITY CLAIM

The present application claims the benefit of U.S. Provisional Patent Application Ser. No. 61/261,310, filed Nov. 14, 2009; the present application also claims the benefit of U.S. Provisional Application Ser. No. 61/293,932, filed Jan. 11, 2010; the present application also claims the benefit of U.S. Provisional Application Ser. No. 61/315,018, filed Mar. 18, 2010; all of the foregoing applications are incorporated herein by reference in their entireties.

BACKGROUND OF THE INVENTION

The present invention is directed to a surgical device. The present invention is more particularly directed to a surgical device for use in robotic surgery, such as for example, in robotic neurosurgery. Still further, the device permits access to surgical sites that may be most desirably accessed over a curvilinear path.

Surgery has typically involved obtaining access to a region that exposes many aspects of a lesion (e.g. tumor, aneurysm, etc.) allowing its treatment or complete dissection and removal. However, obtaining access to the lesion may also involve damage to areas of the brain or other tissues that are normal. In view of the foregoing, a movement has developed to perform what is called "Minimally Invasive Surgery." Unfortunately, this, in many instances, is a misnomer since the surgery may or may not be "minimally invasive" both to the critical tissues under consideration, but also to collateral tissues at the site of entry or along the access path. A better term for this type of surgery is "Minimal Access Surgery." Examples of such surgery include: Endoscopic Surgery, Endoscope Assisted Surgery, Endovascular Surgery, Stereotactic Radiosurgery, etc.

It is often necessary to treat brain tumors and aneurysms in the base of the skull. These are very difficult to treat because accessing the skull base requires disruption of many important structures. It is desirable to minimize the size of any opening to be made through the skull and surrounding, healthy tissues so that pathology in the skull base is treated with the least amount of potential damage to surrounding tissues. Such a procedure could be thought of as "Minimally Disruptive Surgery." Current endoscopic and endoscope-assisted operations performed on the head, skull base, chest, abdomen, and other areas are done with rigid and straight endoscopes and tools that can only work in a straight line. However, in complex areas such as the brain, the endoscope has to negotiate many obstacles en route (e.g. bone, brain, and blood vessels). This imposes significant restrictions on the surgery being performed and can lead to an increase in collateral tissue damage, due to enlarging the access path and/or damaging or sacrificing the control over the structures near the lesion. Additionally, there are certain types of surgery that are at present not possible given the limitations posed by existing technology.

On the other hand, today's endovascular surgery is often performed over comparatively great distance, and by navigating through a variety of curved channels. Such surgery uses a system of coaxial tubes and actuation cables that work on the basis of forward and backward movement, and side-to-side movement. Such devices are used with real-time imaging that guides the operator to the target. A similar approach is used with flexible endoscopes that work inside the gastrointestinal tract. However, these methods are not applicable for microscale surgeries, as are performed for intricate neurosurgeries.

In addition to the foregoing, it is sometimes desirable during surgical procedures to irrigate a surgical site, clean surgical tools, or repeatedly remove and re-introduce surgical tools. This presents a problem with currently known robotic surgical systems because removal of the entire system is generally required to change tools.

The present invention overcomes these and other challenges. It provides a surgical device capable of steering surgical tools to surgical sites over curvilinear neurosurgery paths to avoid unnecessary damage to sensitive or critical collateral tissue. The device is capable of steering surgical tools around anatomical obstacles while affording the tools complete maneuverability at the surgical site and removal/replacement during neurosurgical procedures.

SUMMARY

In one embodiment of the invention, a surgical device comprises an external sheath having a proximal end and a distal end for insertion through an opening of a body and a plurality of tool components extending from the distal end of the external sheath. The tool components are independently deflectable with respect to each other and with respect to the external sheath and removable from the device without requiring straightening or withdrawal of the sheath through the opening of the body.

The device may further include a deflection control assembly that controls the deflection of the tool components from the proximal end of the external sheath. The deflection control assembly may comprise a deflectable tool support associated with and arranged to receive at least one of the tool components so that deflection of the deflectable tool support causes its associated tool component to be deflected. The deflectable tool support may comprise a coil spring. The deflection control assembly may comprise a plurality of pull cables that extend from the deflectable tool support to the proximal end of the external sheath.

The device may further comprise a joy stick at the proximal end of the external sheath and coupled to the plurality of pull cables.

The device may further comprise a support base that supports the deflectable tool support. The support base is movable beyond the distal end of the external sheath. The support base is biased to project outward from the external sheath when moved beyond the distal end of the external sheath.

The device may further include a flexible guide tube associated with each of the deflectable tool supports that runs from the proximal end of the device to the distal end of the device. The guide tubes may be used to remove and reinsert tool components during a procedure without requiring the device to be straightened or removed from the patient.

Each of the tool components may include an elongated flexible shaft that extends proximally from the distal end of the external sheath, through the external sheath and out the proximal end of the external sheath. Each tool component is thus removable from the device by removal of its elongated flexible shaft from the proximal end of the external sheath.

Tool components may include mechanical instruments including, without limitation, graspers, shears, biopsy forceps, and clip appliers. Tool components may also include electrical instruments including, without limitation, electrocautery devices, lasers, and high-intensity focused ultrasound (HIFU) fibers. Tool components may also include other equipment or implantable devices including, without limitation, aneurysm clips, fibrin glue, radioactive seeds for tumors, chemotherapeutic wafers, gel injections, shunts, reservoirs for medication delivery, nano-particle conjugates, future downsized ultrasound tips, and/or other foreign bodies.

The external sheath is flexible and deflectable intermediate the distal and proximal ends. This permits the device to be steered in a curvilinear manner towards a surgical target.

The device may further comprise a flexible guidance tube arranged to receive a tool component and that allows for removal and reinsertion of the tool component without requiring the device to be straightened or removed from the body. The flexible guidance tube may be arranged to facilitate suction and irrigation of the surgical site, with or without removal of the tool component. The flexible guidance tube may be further arranged to facilitate the cleaning of the tool component without requiring removal of the tool component.

The device may further comprise a plurality of sliding control rings at the proximal end of the external sheath that control the deflection of the flexible portion of the sheath.

The device may further comprising a joystick at the proximal end of the sheath. Control of the deflectable degrees of freedom of the device may be divided between the sliding control rings and the joystick.

According to another embodiment, a surgical device comprises an external sheath having a proximal end and a distal end for insertion through an opening of a body. The sheath is flexible and bendable intermediate the distal end and proximal end. The device further includes a plurality of tool components extending from the distal end of the external sheath. The tool components are independently deflectable with respect to each other and with respect to the external sheath.

According to a still further embodiment, a surgical device comprises an external sheath having a proximal end and a distal end for insertion through an opening of a body. The sheath is flexible and bendable intermediate the distal end and the proximal end. The device further includes a plurality of tool components extending from the distal end of the external sheath. The tool components are independently deflectable with respect to each other and with respect to the external sheath. The tool components are also removable from the device without requiring straightening or withdrawal of the sheath through the opening of the body.

BRIEF DESCRIPTION OF THE DRAWINGS

The features of the present invention which are believed to be novel are set forth with particularity in the appended claims. The invention, together with further features and advantages thereof, may best be understood by making reference to the following description taken in conjunction with the accompanying drawings, in the several figures of which like reference numerals identify identical elements, and wherein:

DETAILED DESCRIPTION

Figure 1:
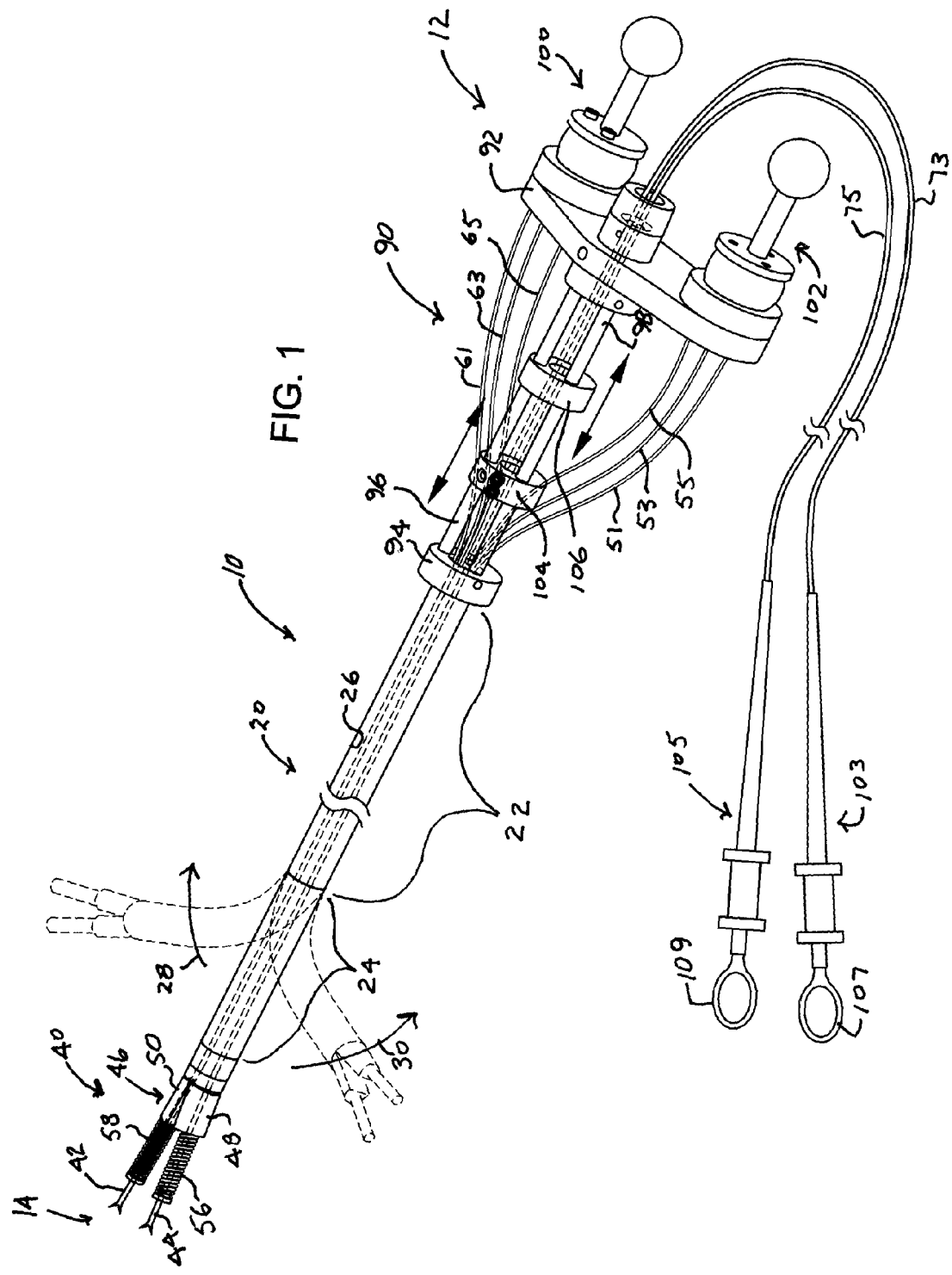
FIG. 1 is perspective view of a surgical device embodying the present invention.

FIG. 1 shows a surgical device 10 embodying the present invention. The device generally includes an external sheath 20, a deflection control assembly 40, and a controller 90. The device 10 has a proximal end 12 and a distal end 14.

The sheath 20 has a substantially rigid portion 22 and a flexible portion 24. The sheath has an internal channel 26 that permits surgical tool components and control cables to pass there through as described subsequently. The flexible portion 24 of the sheath 10 is bendable or steerable between the proximal end 12 and the distal end 14 as indicated by arrows 28 and 30 to render the distal end 14 of device 10 steerable. This allows the distal end 14 to be directed in a curvilinear manner once inserted through an opening of a body and advanced towards a surgical target. This is particularly advantageous for use in surgeries wherein advancement of the sheath around sensitive or vital tissue or anatomical structures is required.

Figure 5:
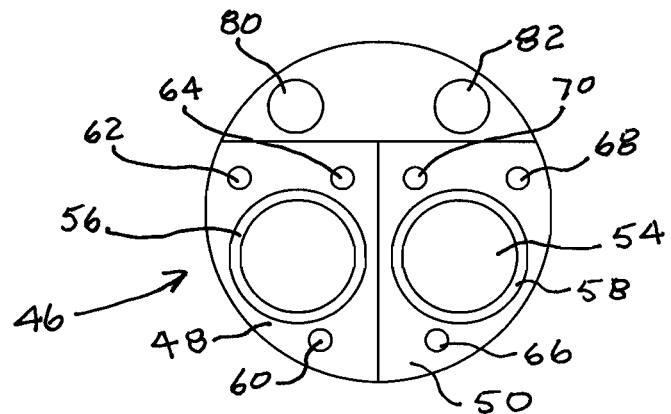
FIG. 5 is a plane end view of the head assembly at the distal end of the device FIG. 1.

The controller 90 at the proximal end 12 of the device 10 is arranged to control the steering movement of the flexible portion 24 of the sheath 20, the general placement of the tools 42 and 44 at the distal end 14, and the movement of the tools 42 and 44, once placed. With respect to the general placement of the tools, the end view of FIG. 5 shows a head assembly at the distal end of the sheath 20.

The head assembly includes tool supports 48 and 50. Each tool support includes a channel for receiving a tool. To that end, the tool support 48 includes tool channel 52 and tool support 50 includes tool channel 54. Each tool support also includes a coiled spring. To that end, tool support 48 includes coiled spring 56 and tool support 50 includes coiled spring 58. While cutting tool components are illustrated herein, it is to be understood that other tool components may be controlled as well including visualization tools, other surgical tools and suction/irrigation tools, for example. Each tool support also makes provision for at least three pull cables to deflect the coiled springs 56 and 58. To this end, tool support 48 includes cable channels 60, 62, and 64, and tool support 50 includes cable channels 66, 68, and 70.

The head assembly 46 also makes provision for visualization during a surgical procedure. To this end, the head assembly further includes channels 80 and 82. One of channels 80 or 82 may accommodate a light source, such as a fiber optic cable, for example, while the other of the channels 80 or 82 may accommodate a camera. The light source and camera may also be incorporated into a single device occupying one of the channels 80 or 82, and allowing the other of the channels 80 or 82 to be occupied by an alternate device such as a suction or irrigation tube or a cauterizing fiber.

Figure 2:
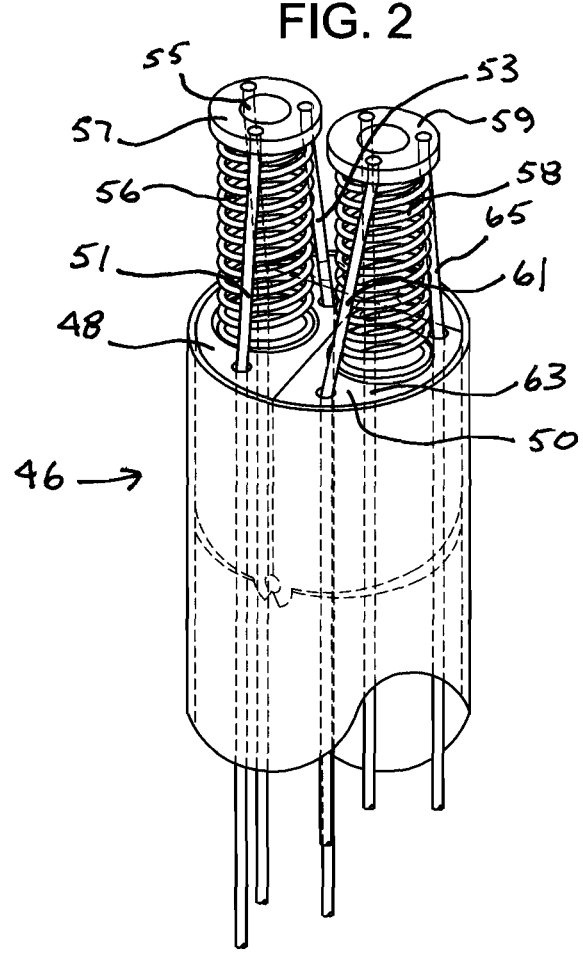
FIG. 2 is a perspective view, to an enlarged scale, of a deflection control assembly that may be employed to impart deflection control of a pair of surgical instruments according to one embodiment of the invention.

FIG. 2 shows the head assembly 46 in perspective and to an enlarged scale. Here it may be seen the coiled spring 56 terminates with a ring member 57 and coiled spring 58 terminates with a ring member 59. The aforementioned pull cables are attached to the ring members 57 and 59. For example, pull cables 51, 53, and 55 are attached to ring 57 of coiled spring 56. Similarly, pull cables 61, 63, and 65 are attached to ring 59 of coiled spring 58. The pull cables extend from their associated coiled springs, through the cable channels and proximally to the controller 90.

Referring again to FIG. 1, the controller 90 includes a controller base 92 that is fixed with respect to the rigid portion 22 of the sheath 20. A controller adapter 94 is secured to the rigid portion 22 of the sheath 20. It is also secured to the controller base by a pair of rails 96 and 98. The controller base carries a pair of joy stick controls 100 and 102. The joy stick controls control the pulling on the pull cables 51, 53, and 55 and 61, 63, and 65 associated with coiled springs 56 and 58, respectively. As may be seen in FIG. 1, pull cables 51, 53, and 55 associated with coiled spring 56 are couple to joy stick 102. Similarly, pull cables 61, 63, and 65 are coupled to joy stick 100. Hence, joy stick 102 controls the deflection of coiled spring 56 and joy stick 100 controls the deflection of coiled spring 58.

Figure 3:
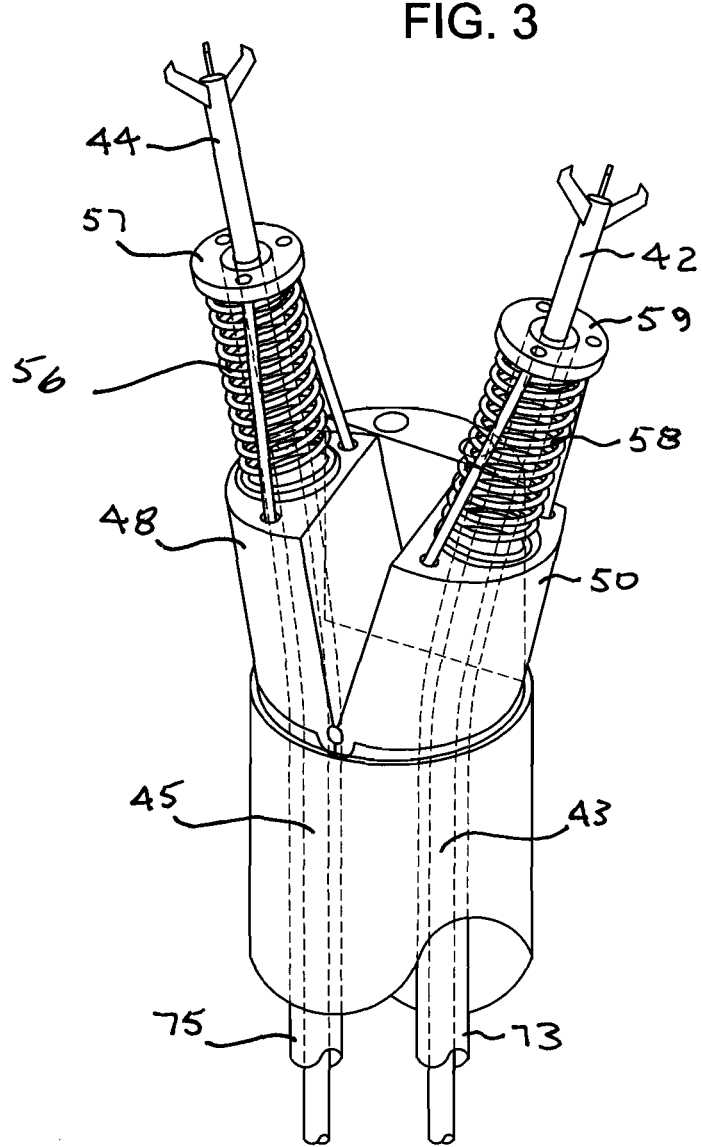
FIG. 3 is a perspective view, to an enlarged scale, of the deflection control assembly of FIG. 2 after receiving a pair of surgical instruments according to one embodiment of the invention.
Figure 6:
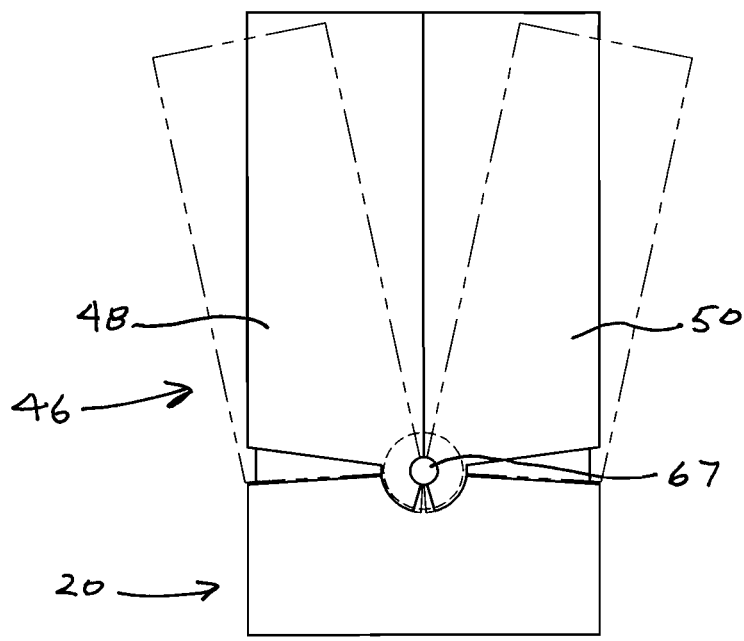
FIG. 6 is a side view of the tool support bases illustrating a manner in which the support bases may be projected outward upon being moved distally to the sheath distal end.

FIG. 3 shows surgical tool components 44 and 42 being received by the coiled springs 56 and 58 respectively. The tool supports 48 and 50 are projecting outwardly to separate the tools 44 and 42. As best seen in FIG. 6, the tool supports 48 and 50 are mounted for pivotal movement about a pivot axis 67. The tool supports 48 and 50 are biased to project outwardly. The bias may be provided in the tool supports, for example, by the shape of the tool supports, as in a slight interference fit between the tool supports to cause their separation.

As may be seen in FIG. 3, with coil spring 56 receiving tool 44, any deflection in coil spring 56 by joy stick 102 (FIG. 1) will impart a similar deflection in tool 44. Similarly, with coil spring 58 receiving tool 42, any deflection in coil spring 58 by joy stick 100 (FIG. 1) will impart a similar deflection in tool 42. In this manner, the general placement of tools 42 and 44 may be controlled. Hence, the tool supports and coiled springs form deflection control assemblies for deflecting their associated tools.

As may also be seen in FIG. 3, each tool includes a flexible shaft. To this end, tool 44 includes flexible shaft 45 and tool 42 includes flexible shaft 43. The shafts 43 and 45 extend through flexible guide tubes 73 and 75, respectively. The guide tubes 73 and 75 extend from the rings 59 and 57, respectively, proximally out the proximal end of the sheath 20 to finger loop interfaces 103 and 105, respectively. Such interfaces are well known in the art. The control loops 107 and 109 are coupled to the flexible tool shafts 43 and 47. The tools 42 and 44 are thus removable from the device by the pulling of the flexible tool shafts 43 and 45 out of the guide tubes 73 and thus out of the device. Hence, the tools 42 and 44 are removable from the device without the device having to be straightened or removed from the patient. This facilitates ready cleaning of the tools or replacement of the tools with similar or different tools.

The guides tubes 73 and 75, in addition to providing guidance of the tools 42 and 44 and the tool shafts 43 and 45 may also perform other functions. For example, one or both guide tubes may be used for irrigation and/or suction at the surgical site. The guide tubes may have a cross-sectional dimension greater than the cross-sectional dimension of the tools. Thus, when a tool is within a guide tube, a space running along the tube between the tube and the tool is provided. The guide tubes may thus be used for irrigation and/or suction with or without the tool components in place. With the tool components in place, irrigation can also be used to clean the tool tips without requiring their removal.

Figure 4:
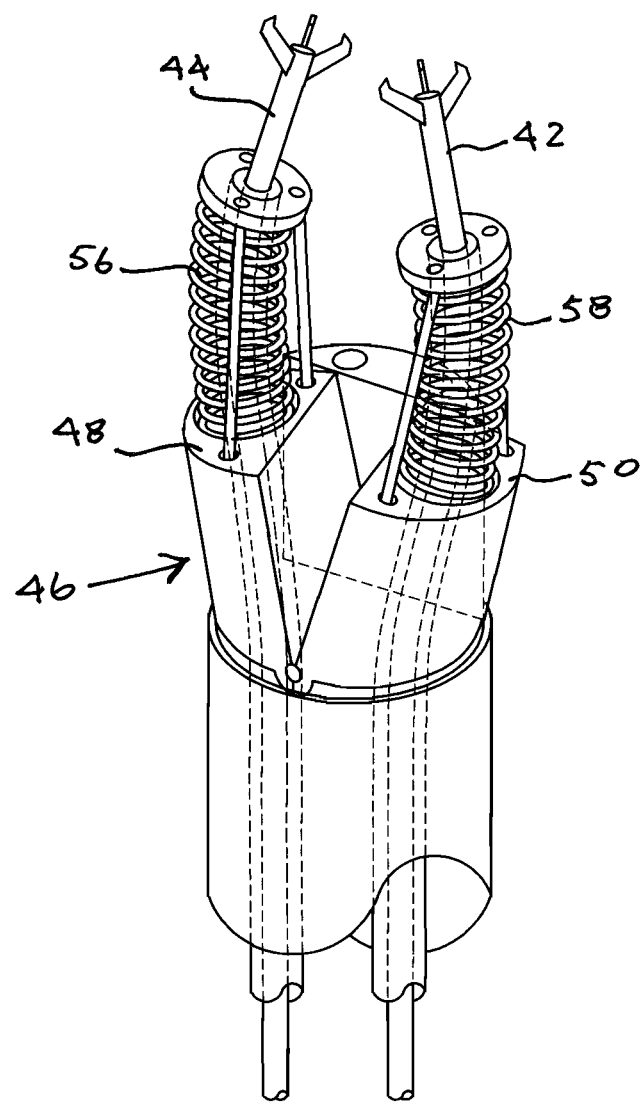
FIG. 4 is a perspective view, to an enlarged scale, of the deflection control assembly of FIG. 2 controlling the positioning of the pair of surgical instruments according to one embodiment of the invention.

FIG. 4 shows that once the tools 42 and 44 are separated, they may be manipulated, as by being brought together, by the deflection of the coil springs 56 and 58 facilitated by the operation of the joy sticks 100 and 102. Once the tools 42 and 44 are at the surgical site through general placement of each tool 42 and 44, the tools may be rotated or moved in and out by operation of its associated control ring 107 and 109.

The flexing of the flexible portion 24 of the sheath 20 may be controlled by sliding control rings 104 and 106. The rings 104 and 106 are arranged to slide along rails 96 and 98 (a third rail is not visible in FIG. 1, as it is hidden by the flexible tool shafts). Each one of rings 104 and 106 is coupled to a control cable (not shown) that is connected to the inside wall of the flexible portion 24 of the sheath 20. Pulling or pushing on one of the rings causes the flexible portion 24 of the sheath to deflect in one plane, while pulling or pushing on the other one of the rings causes the flexible portion 24 of the sheath 20 to deflect in a perpendicular plane. In this manner, the device may be steered along a curvilinear path to the surgical site.

As may be seen from the foregoing, the present invention provides an improved surgical device that permits surgical instruments to reach remote portions of the body with reduced trauma. The device sheath may be steered to a surgical site around sensitive or critical tissue. The surgical tool components may be removed for replacement or cleaning without the device having to be straightened or removed from the body. Further, the tool deflection assemblies and methodology renders precise control of the surgical tool components in all required degrees and directions of movement. The present invention is thus well suited for use in many different applications, including robotic surgical systems.

While a particular embodiment of the invention has been shown and described, changes and modifications may be made. It is therefore intended to cover in the appended claims all such changes and modifications which fall within the true spirit and scope of the invention.

What is claimed is:

1. A surgical device, comprising:
   an external sheath having a proximal end and a distal end for insertion through an opening of a body; and a plurality of tool components extending from the distal end of the external sheath, the tool components being independently deflectable with respect to each other and with respect to the external sheath and removable from the device without requiring withdrawal of the sheath through the opening of the body, and including a deflection control assembly that controls the deflection of the tool components from the proximal end of the external sheath,
   wherein the deflection control assembly comprises a plurality of deflectable tool supports at the distal end of the external sheath, the plurality of deflectable tool supports associated with and arranged to each receive at least one of the tool components whereby deflection of the respective deflectable tool support causes its associated tool component to be deflected,
   the device further comprising a plurality of tool supports each containing a deflectable tool support extending therefrom, the plurality of tool supports hingedly connected to each other about a pivot axis at a proximal end of each of the tool supports and biased against one another such that the plurality of tool supports project radially outwardly from the external sheath without connection to each other beyond a proximal end of each of the plurality of tool support when the plurality of tool supports are moved beyond the distal end of the external sheath.

2. The device of claim 1, wherein the deflectable tool support comprises a coil spring.

3. The device of claim 1, further comprising a flexible guidance tube arranged to receive a tool component and that allows for removal and reinsertion of the tool component without requiring the device to be straightened or removed from the body.

4. The device of claim 3, wherein the flexible guidance tube is arranged to facilitate suction and irrigation of the surgical site, with or without removal of the tool component.

5. The device of claim 3, wherein the flexible guidance tube is further arranged to facilitate the cleaning of the tool component without requiring removal of the tool component.

6. The device of claim 1, wherein the deflection control assembly comprises a plurality of pull cables that extend from the deflectable tool support to the proximal end of the external sheath.

7. The device of claim 6, further comprising a joy stick at the proximal end of the external sheath and coupled to the plurality of pull cables.

8. The device of claim 1, wherein each of the tool components includes an elongated flexible shaft that extends proximally from the distal end of the external sheath, through the external sheath, and out the proximal end of the external sheath, and wherein each tool component is removable from the device by removal of its elongated flexible shaft from the proximal end of the external sheath.

9. The device of claim 1, wherein the external sheath is flexible and deflectable intermediate the distal and proximal ends.

10. The device of claim 9, further comprising a plurality of sliding control rings at the proximal end of the external sheath that control the deflection of the flexible portion of the sheath.

11. The device of claim 10, further comprising a joy stick at the proximal end of the sheath, wherein control of the deflectable degrees of freedom of the device is divided between the sliding control rings and the joy stick.

12. A surgical device, comprising:
an external sheath having a proximal end and a distal end for insertion through an opening of a body and being flexible and bendable between the distal end and proximal end; and
a plurality of tool components extending from the distal end of the external sheath, the tool components being independently deflectable with respect to each other and with respect to the external sheath, and including a deflection control assembly that controls the deflection of the tool components from the proximal end of the external sheath,
wherein the deflection control assembly comprises a plurality of deflectable tool supports at the distal end of the external sheath, the plurality of deflectable tool supports associated with and arranged to each receive at least one of the tool components whereby deflection of the respective deflectable tool support causes its associated tool component to be deflected,
the device further comprising a plurality of tool supports each containing a deflectable tool support extending therefrom, the plurality of tool supports biased against one another such that the plurality of tool supports projects radially outwardly from the external sheath without connection to each other beyond a proximal end of each of the plurality of tool supports when the plurality of tool supports are moved beyond the distal end of the external sheath.

13. The device of claim 12, wherein the deflectable tool support comprises a coil spring.

14. The device of claim 12, further comprising a flexible guidance tube arranged to receive a tool component and that allows for removal and reinsertion of the tool component without requiring the device to be straightened or removed from the body.

15. The device of claim 14, wherein the flexible guidance tube is arranged to facilitate suction and irrigation of the surgical site, with or without removal of the tool component.

16. The device of claim 14, wherein the flexible guidance tube is further arranged to facilitate the cleaning of the tool component without requiring removal of the tool component.

17. The device of claim 12, wherein the deflection control assembly comprises a plurality of pull cables that extend from the deflectable tool support to the proximal end of the external sheath.

18. The device of claim 17, further comprising a joy stick at the proximal end of the external sheath and coupled to the plurality of pull cables.

19. The device of claim 12, wherein each of the tool components includes an elongated flexible shaft that extends proximally from the distal end of the external sheath, through the external sheath, and out the proximal end of the external sheath, and wherein each tool component is removable from the device by removal of its elongated flexible shaft from the proximal end of the external sheath.

20. The device of claim 12, further comprising a plurality of sliding control rings at the proximal end of the external sheath that control the deflection of the flexible portion of the sheath.

21. The device of claim 20, further comprising a joy stick at the proximal end of the sheath, wherein control of the deflectable degrees of freedom of the device is divided between the sliding control rings and the joy stick.

22. The device of claim 12 wherein the plurality of tool supports are hingedly connected to each other about a pivot axis at a proximal end of each of the tool supports.

23. A surgical device, comprising:
an external sheath having a proximal end and a distal end for insertion through an opening of a body and being flexible and bendable between the distal end and the proximal end; and
a plurality of tool components extending from the distal end of the external sheath, the tool components being independently deflectable with respect to each other and with respect to the external sheath and removable from the device without requiring withdrawal of the sheath through the opening of the body, and including a deflection control assembly that controls the deflection of the tool components from the proximal end of the external sheath, wherein the deflection control assembly comprises the plurality of deflectable tool supports at the distal end of the external sheath, the plurality of deflectable tool supports associated with and arranged to each receive at least one of the tool components whereby deflection of the respective deflectable tool support causes its associated tool component to be deflected,
the device further comprising plurality of tool supports each containing a deflectable tool support extending therefrom, the plurality of tool supports biased against one another such that the plurality of tool supports projects radially outwardly from the external sheath without connection to each other beyond a proximal end of each of the plurality of tool supports when the plurality of tool supports are moved beyond the distal end of the external sheath.

24. The device of claim 23 wherein the plurality of tool supports are hingedly connected to each other about a pivot axis at a proximal end of each of the tool supports.

25. A surgical device, comprising:
an external sheath having a proximal end and a distal end for insertion through an opening of a body; and
a plurality of tool components extending from the distal end of the external sheath, the tool components being independently deflectable with respect to each other and with respect to the external sheath and removable from the device without requiring withdrawal of the sheath through the opening of the body, and including a deflection control assembly that controls the deflection of the tool components from the proximal end of the external sheath, and wherein the deflection control assembly comprises a plurality of pull cables that extend from a deflectable tool support to the proximal end of the external sheath, wherein the plurality of pull cables also extend through a tool support located at the distal end of the external sheath and holding the deflectable tool support wherein the plurality of pull cables are spaced apart from the deflectable tool support on the tool support and extend externally from the tool support to a distal end of the deflectable tool support,
the device further comprising plurality of tool supports each containing a deflectable tool support extending therefrom, the plurality of tool supports biased against one another such that the plurality of tool supports projects radially outwardly from the external sheath without connection to each other beyond a proximal end of each of the plurality of tool supports when the plurality of tool supports are moved beyond the distal end of the external sheath.

26. The device of claim 25, wherein the deflection control assembly comprises the deflectable tool support associated with and arranged to receive at least one of the tool components whereby deflection of the deflectable tool support causes its associated tool component to be deflected.

27. The device of claim 26, wherein the deflectable tool support comprises a coil spring.

28. The device of claim 26, further comprising a flexible guidance tube arranged to receive a tool component and that allows for removal and reinsertion of the tool component without requiring the device to be straightened or removed from the body.

29. The device of claim 28, wherein the flexible guidance tube is arranged to facilitate suction and irrigation of the surgical site, with or without removal of the tool component.

30. The device of claim 28, wherein the flexible guidance tube is further arranged to facilitate the cleaning of the tool component without requiring removal of the tool component.

31. The device of claim 30, further comprising a joy stick at the proximal end of the external sheath and coupled to the plurality of pull cables.

32. The device of claim 26, further comprising the tool support that supports the deflectable tool support, the tool support being movable beyond the distal end of the external sheath.

33. The device of claim 25, wherein each of the tool components includes an elongated flexible shaft that extends proximally from the distal end of the external sheath, through the external sheath, and out the proximal end of the external sheath, and wherein each tool component is removable from the device by removal of its elongated flexible shaft from the proximal end of the external sheath.

34. The device of claim 25, wherein the external sheath is flexible and deflectable intermediate the distal and proximal ends.

35. The device of claim 34, further comprising a plurality of sliding control rings at the proximal end of the external sheath that control the deflection of the flexible portion of the sheath.

36. The device of claim 35, further comprising a joy stick at the proximal end of the sheath, wherein control of the deflectable degrees of freedom of the device is divided between the sliding control rings and the joy stick.

37. The device of claim 25 wherein a plurality of tool supports are hingedly connected to each other about a pivot axis at a proximal end of each of the tool supports.

38. A surgical device, comprising:
an external sheath having a proximal end and a distal end for insertion through an opening of a body and being flexible and bendable between the distal end and proximal end; and
a plurality of tool components extending from the distal end of the external sheath, the tool components being independently deflectable with respect to each other and with respect to the external sheath, and including a deflection control assembly that controls the deflection of the tool components from the proximal end of the external sheath; and wherein the deflection control assembly comprises a plurality of pull cables that extend from a deflectable tool support to the proximal end of the external sheath, wherein the plurality of pull cables also extend through a tool support located at the distal end of the external sheath and holding the deflectable tool support wherein the plurality of pull cables are spaced apart from deflectable tool support on the tool support and extend externally from the tool support to a distal end of the deflectable tool support,
the device further comprising plurality of tool supports each containing a deflectable tool support extending therefrom, the plurality of tool supports biased against one another such that the plurality of tool supports projects radially outwardly from the external sheath without connection to each other beyond a proximal end of each of the plurality of tool supports when the plurality of tool supports are moved beyond the distal end of the external sheath.

39. The device of claim 38, wherein the deflection control assembly comprises the deflectable tool support associated with and arranged to receive at least one of the tool components whereby deflection of the deflectable tool support causes its associated tool component to be deflected.

40. The device of claim 39, wherein the deflectable tool support comprises a coil spring.

41. The device of claim 38, further comprising a flexible guidance tube arranged to receive a tool component and that allows for removal and reinsertion of the tool component without requiring the device to be straightened or removed from the body.

42. The device of claim 41, wherein the flexible guidance tube is arranged to facilitate suction and irrigation of the surgical site, with or without removal of the tool component.

43. The device of claim 41, wherein the flexible guidance tube is further arranged to facilitate the cleaning of the tool component without requiring removal of the tool component.

44. The device of claim 38, further comprising a joy stick at the proximal end of the external sheath and coupled to the plurality of pull cables.

45. The device of claim 38, wherein each of the tool components includes an elongated flexible shaft that extends proximally from the distal end of the external sheath, through the external sheath, and out the proximal end of the external sheath, and wherein each tool component is removable from the device by removal of its elongated flexible shaft from the proximal end of the external sheath.

46. The device of claim 38, further comprising a plurality of sliding control rings at the proximal end of the external sheath that control the deflection of the flexible portion of the sheath.

47. The device of claim 46, further comprising a joy stick at the proximal end of the sheath, wherein control of the deflectable degrees of freedom of the device is divided between the sliding control rings and the joy stick.

48. The device of claim 38 wherein a plurality of tool supports are hingedly connected to each other about a pivot axis at a proximal end of each of the tool supports.

49. A surgical device, comprising:
an external sheath having a proximal end and a distal end for insertion through an opening of a body and being flexible and bendable between the distal end and the proximal end; and a plurality of tool components extending from the distal end of the external sheath, the tool components being independently deflectable with respect to each other and with respect to the external sheath and removable from the device without requiring withdrawal of the sheath through the opening of the body the device further comprising a plurality of tool supports each containing a deflectable tool component extending therefrom, the plurality of tool supports configured to cause the plurality of tool supports to project radially outwardly from the external sheath without connection to each other beyond a proximal end of each of the plurality of tool supports when the plurality of tool supports are moved beyond the distal end of the external sheath, the device further comprising plurality of tool supports each containing a deflectable tool support extending therefrom, the plurality of tool supports biased against one another such that the plurality of tool supports projects radially outwardly from the external sheath without connection to each other beyond a proximal end of each of the plurality of tool supports when the plurality of tool supports are moved beyond the distal end of the external sheath.

50. The device of claim 49 wherein the plurality of tool supports are hingedly connected to each other about a pivot axis at a proximal end of each of the tool supports.

* * * * *